US00PP37536P3

(12) United States Plant Patent

Lee et al.

(10) Patent No.: US PP37,536 P3
(45) Date of Patent: Jul. 21, 2026

(54) *CATHARANTHUS* PLANT NAMED 'CARZ0007'

(50) Latin Name: *Catharanthus roseus*
Varietal Denomination: CARZ0007

(71) Applicant: SYNGENTA CROP PROTECTION AG, Basel (CH)

(72) Inventors: Jaemin Lee, Gilroy, CA (US); Jaqueline Fregoso, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 19/378,966

(22) Filed: Nov. 4, 2025

(65) Prior Publication Data

US 2026/0130306 P1 May 7, 2026

(30) Foreign Application Priority Data

Nov. 7, 2024 (CA) ..... CA24-11874

(51) Int. Cl.
*A01H 5/02* (2018.01)
*A01H 6/08* (2018.01)

(52) U.S. Cl.
USPC ..... Plt./263.1
CPC ..... *A01H 6/084* (2018.05); *A01H 5/02* (2013.01)

(58) Field of Classification Search
USPC ..... Plt./263.1
CPC ..... A01H 6/084; A01H 5/02
See application file for complete search history.

*Primary Examiner* — Keith O. Robinson
(74) *Attorney, Agent, or Firm* — Dale Skalla

(57) ABSTRACT

'CARZ0007' is a product of a planned breeding program. The new cultivar 'CARZ0007' has medium-strong red colored flowers, excellent flower production, moderate plant size and uniform mounding and semi-spreading habit with medium green foliage.

1 Drawing Sheet

Latin name of the genus and species of the plant claimed: *Catharanthus roseus.*

DETAILED DESCRIPTION

*Catharanthus* variety 'CARZ0007' disclosed in the present application has shown uniformity and stability, as described in the following section. *Catharanthus* variety 'CARZ0007' disclosed in the present application has been asexually reproduced by a sufficient number of generations with careful attention to uniformity of plant type and has been increased with continued observation for uniformity.

ORIGIN OF 'CARZ0007'

'CARZ0007' is a product of a planned breeding program. The new cultivar 'CARZ0007' has medium-strong red colored flowers, excellent flower production, moderate plant size and uniform mounding and somewhat spreading habit with medium green foliage.

The variety 'CARZ0007' was derived through vegetative propagation from the parent plant designated as 'CATFN1525-1', (not patented). The parent plant resulted from a controlled self-pollination conducted in March 2019 in a controlled greenhouse environment in Gilroy, California. The parent plant exhibited distinctive characteristics including medium-sized flowers displaying medium-strong red colored flowers and demonstrated a semi-cascade growth habit.

The seed was sown in March 2021 in a greenhouse in Gilroy, California. 'CARZ0007' was selected as a single flowering plant in September 2021.

The first act of asexual reproduction of 'CARZ0007' was accomplished when vegetative stem cuttings were propagated from the initial selection in January 2022 in a greenhouse in Gilroy, California.

Horticultural examination of plants grown from cuttings of the original plant in January 2022, in Gilroy, California, and continuing thereafter, has demonstrated that the combination of characteristics as herein disclosed for 'CARZ0007' are firmly fixed and are retained through successive generations of asexual reproduction.

'CARZ0007' has not been observed under all possible environmental conditions. The phenotype may vary significantly with variations in environment such as temperature, light intensity, disease exposure, and day length.

A Plant Breeder's Right for this cultivar was applied for in Canada on Nov. 7, 2024, No. 24-11874. 'CARZ0007' has not been made publicly available prior to the effective filing date of this application, notwithstanding any disclosure that may have been made less than one year prior to the effective filing date of this application by the inventor or another who obtained 'CARZ0007' directly from the inventor.

The plant descriptions and measurements were taken in Gilroy, California in October 2025. The plants were approximately 40 weeks old and were growing in 4.5" pots grown in a greenhouse.

TABLE 1

DIFFERENCES BETWEEN THE NEW VARIETY 'CARZ0007' AND A MOST SIMILAR VARIETY

| | 'CARZ0007' | 'Titan ™ Dark Red, Not patented |
|---|---|---|
| Flower color: | Medium-strong red colored flowers consistently throughout | Strong red colored flowers consistently throughout |
| Disease resistance: | Known disease resistance to *Phytophthora nicotianae* | No known disease resistance to *Phytophthora nicotianae* |
| Plant habit: | Mounded and somewhat spreading | Mounded and compact |

Figure 1:
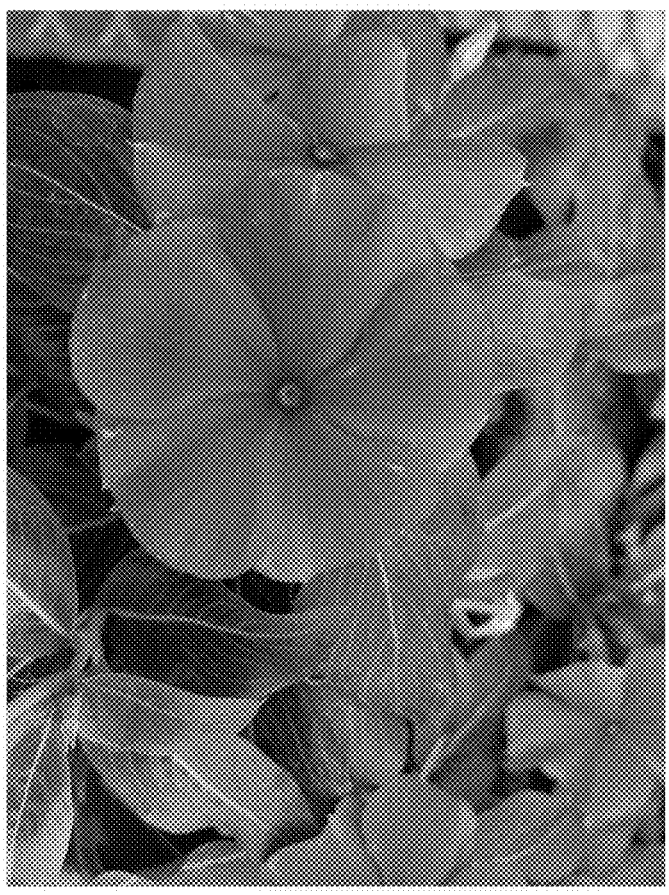
FIG. 1 shows a close view of an inflorescence. Taken on Feb. 14, 2022 in Gilroy, California.
Figure 2:
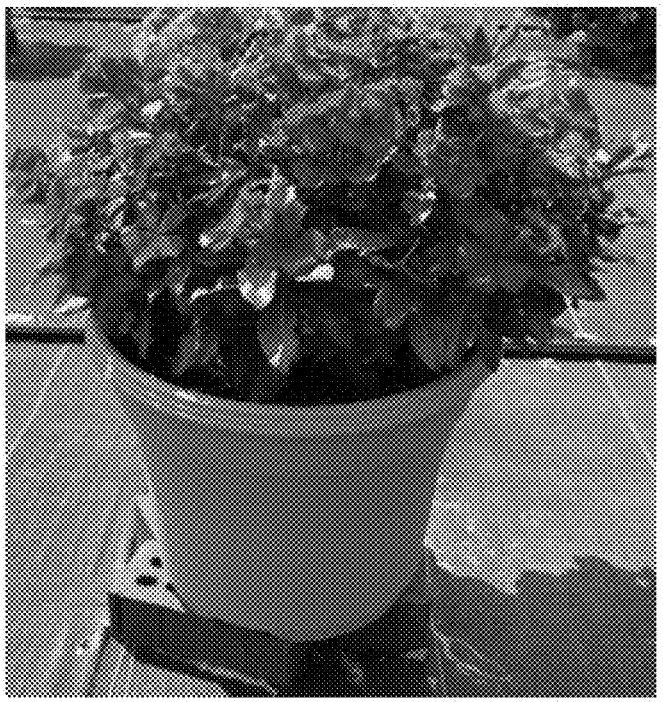
FIG. 2 shows a whole flowering plant. Taken on Sep. 8, 2022 in Gilroy, California. The plant was approximately 138 days old and were growing in a 14" pot outdoors.

The plant descriptions and measurements were taken in Gilroy, California in October 2025. The plants were approximately 40 weeks old and were growing in 4.5" pots grown in a greenhouse.

Color references and designations made herein are based upon The Royal Horticultural Society Colour Chart, Second edition (1986, London & Leiden: Royal Horticultural Society & Flower Council of Holland).

*Form, growth and habit.*—Semi-woody, grown as an annual; mounding and Somewhat spreading habit; very well branched.
*Plant height.*—24 cm.
*Plant height* (*inflorescence included*).—25 cm.
*Plant width.*—30 cm.

Foliage:
*Type.*—Opposite.
*Immature, leaf color, upper surface.*—Closest to RHS 144A.
*Lower surface.*—Closest to RHS 146B.
*Mature, leaf color, upper surface.*—Closest to RHS 141A.
*Lower surface.*—Closest to RHS 143A.
*Vein color, upper surface.*—Closest to RHS 145A.
*Vein color, lower surface.*—Closest to RHS 145D.
*Length.*—10.0-13.0 cm.
*Width.*—2.5-4.5 cm.
*Shape.*—Ovate.
*Base shape.*—Acute.
*Apex shape.*—Acuminate.
*Margin.*—Entire.
*Texture, upper.*—Smooth.
*Texture, lower surface.*—Smooth.
*Pattern of veining.*—Pinnate.
*Petioles color.*—Closest to RHS 142B.
*Petioles length.*—0.4-1.4 cm.
*Diameter of petiole.*—0.20 cm.
*Texture* (*upper and lower surface*).—Smooth.

Stem:
*Color of stem.*—Closest to RHS 142B.
*Length of stem.*—20-25 cm.
*Diameter.*—0.4-0.6 cm.
*Length of internodes.*—3.0-6.5 cm.
*Texture.*—Smooth.
*Average number of stems.*—4-8.

Inflorescence:
*Type.*—Panicle.
*Blooming habit.*—Flowers continuously from spring through fall.
*Number of open flowers per inflorescence.*—About 2-6.
*Quantity of inflorescences per plant.*—About 24-36.
*Lastingness of individual blooms on the plant.*—About 2 weeks (depending on temperatures).
*Fragrance.*—Rose.

Flower:
*Arrangement.*—Arising from upper leaf axils, freely flowering, facing upwards and outwards.
*Floret form.*—Single salverform, tube with disc of petals.
*Petal shape.*—Wedge-shaped.
*Petal arrangement.*—Overlapping.
*Number of petals.*—5 petals.
*Length of floret.*—6.1 cm.
*Width of floret.*—6.1 cm.
*Depth of floret.*—2.8 cm.
*Peduncle length.*—0.3 cm.
*Peduncle diameter.*—0.2 cm.
*Peduncle texture.*—Smooth.
*Peduncle color.*—RHS 141C.
*Petal length.*—2.9 cm.
*Petal width.*—3.0-3.6 cm.
*Flower diameter.*—4.5-5.0 cm.
*Young floret, color upper surface.*—Closest to RHS 44B.
*Young floret, color lower surface.*—Closest to RHS 37C.
*Mature florets, color upper surface.*—Closest to RHS 44B.
*Mature floret, color lower surface.*—Closest to RHS 37C.
*Young floret, color orifice surface.*—Closest to RHS 44A.
*Young mature, color orifice surface.*—Closest to RHS 44A.
*Petal eye zone diameter.*—1 cm.
*Petal eye, color outer surface.*—Closest to RHS 45B.
*Petal eye, color inner surface.*—Closest to RHS 37C.
*Apex shape.*—Wedge-Shaped.
*Degree of lobation.*—Deep.
*Petal margin.*—Entire.
*Base.*—Fused.
*Texture, upper surface.*—Smooth.
*Lower surface.*—Smooth.
*Peduncle, color outer surface.*—Closest to RHS 187C and RHS 145C.
*Peduncle, color inner surface.*—Closest to RHS 145C.
*Peduncle, length.*—2.6-3.0 cm.
*Peduncle, diameter* (*at opening*).—0.19 cm.
*Peduncle, texture outer surface.*—Smooth.
*Peduncle surface.*—Smooth.
*Bract number per flower.*—0.
*Sepal number per flower.*—5.
*Sepal shape.*—Lanceolate.
*Sepal margin.*—Smooth.

Bud (just before opening):
*Color.*—Closest to RHS 51C.
*Length.*—1.8 cm.

*Width.*—0.6 cm at the widest point.
*Shape.*—Tubular.

Bract:
*Color both surfaces.*—Closest to RHS 187C and RHS 145B.
*Length.*—0.7-1.1 cm.
*Diameter.*—0.15-0.2 cm.
*Texture, upper surface.*—Hirsute.
*Lower surface.*—Hirsute.

Calyx:
*Number of sepals.*—5, fused sepals forming a short tube around the base of the floret.
*Color of sepals, upper surface.*—RHS 145A.
*Color of sepals, lower surface.*—RHS 145A.
*Length of sepals.*—0.2-0.3 cm.
*Width of sepals.*—0.1 cm.
*Apex margins.*—Entire.
*Texture, outer surface.*—Pubescent.
*Inner surface.*—Glabrous.

Reproductive organs:

Gynoecium:
*Pistil quantity.*—One.
*Length.*—0.35 cm.
*Style color.*—RHS 159D.
*Style length.*—0.2 cm.
*Stigma color.*—RHS 145C.
*Ovary color.*—RHS 144A.
*Ovary length.*—0.1 cm.
*Ovary diameter.*—0.05 cm.
*Immature, leaf venation, upper surface.*—Closest to RHS 154D.
*Lower surface.*—Closest to RHS 5D.
*Mature, leaf venation, upper surface.*—Closest to RHS 154C.
*Lower surface.*—Closest to RHS 4D.

Androecium:
*Stamen quantity.*—4.
*Color of filaments.*—RHS 159D.
*Length filaments.*—0.05 cm.
*Anther color.*—RHS 164A.
*Length of anthers.*—0.1 cm.
*Color of pollen.*—RHS 10D.
*Pollen amount.*—Moderate.
*Fertility/seed set.*—Moderate.
*Typical seed number.*—10-20.
*Seed length.*—0.3 cm.
*Seed width.*—0.1-0.2 cm.
*Seed color.*—RHS 203A.
*Disease resistance.*—Exhibits strong resistance to aerial *Phytophthora* (*Phytophthora nicotianae*). Insect pest resistance not observed.

Roots:
*Type.*—Fibrous.
*System.*—Well-developed, moderately branched.
*Distribution.*—Spreading laterally and vertically.
*Primary color.*—Closest to RHS 158D.
*Texture.*—Smooth, flexible.
*Average diameter.*—1-2 mm for primary roots.
*Length.*—Not observed.
*Branching pattern.*—Moderately branched with numerous secondary roots.
*Root hairs.*—Present, fine and abundant.

Growing characteristics: The plant has been observed to be hardy in USDA Plant Hardiness Zones 8 through 11.

What is claimed is:

1. A new and distinct cultivar of *Catharanthus* plant named 'CARZ0007', substantially as illustrated and described herein.

* * * * *